United States Patent
Lehmann et al.

(10) Patent No.: US 7,255,836 B2
(45) Date of Patent: Aug. 14, 2007

(54) ANALYTICAL SENSITIVITY ENHANCEMENT BY CATALYTIC TRANSFORMATION

(75) Inventors: Kevin Lehmann, Lawrence, NJ (US); Yu Chen, Hatboro, PA (US); Wen-Bin Yan, Cranbury, NJ (US)

(73) Assignee: Trustees of Princeton University, Princeton, NJ (US)

( * ) Notice: Subject to any disclaimer, the term of this patent is extended or adjusted under 35 U.S.C. 154(b) by 422 days.

(21) Appl. No.: 10/387,911

(22) Filed: Mar. 13, 2003

(65) Prior Publication Data

US 2004/0180448 A1 Sep. 16, 2004

(51) Int. Cl.
- B32B 5/02 (2006.01)
- B32B 27/04 (2006.01)
- B32B 27/12 (2006.01)
- G01N 7/00 (2006.01)
- G01N 21/00 (2006.01)

(52) U.S. Cl. .............. 422/83; 422/94; 422/95; 422/96; 422/97; 422/98; 73/1.01; 73/1.02; 73/23.2; 73/23.31; 436/43; 436/135; 436/136; 436/137; 436/138; 436/159; 436/106; 436/127; 436/139; 436/143; 436/144; 436/149; 29/592; 29/592.1

(58) Field of Classification Search .............. 422/83, 422/94, 95, 96, 97, 98; 73/1.01, 1.02, 23.2, 73/23.31; 436/43, 106, 127, 139, 143, 144, 436/149, 135, 136, 137, 138, 159; 29/592, 29/592.1

See application file for complete search history.

(56) References Cited

U.S. PATENT DOCUMENTS

| | | | |
|---|---|---|---|
| 3,846,340 A * | 11/1974 | Okuyama et al. | 502/84 |
| 3,883,443 A * | 5/1975 | Nakamoto et al. | 502/184 |
| 3,977,836 A | 8/1976 | Matsuda et al. | |
| 4,304,752 A | 12/1981 | Jenkins et al. | |
| 4,992,384 A | 2/1991 | Laurs et al. | |
| 5,528,040 A | 6/1996 | Lehmann | |
| 5,758,491 A * | 6/1998 | Agustin et al. | 60/274 |
| 6,253,548 B1 * | 7/2001 | Ap et al. | 60/320 |

FOREIGN PATENT DOCUMENTS

| | | |
|---|---|---|
| CA | 969166 | 6/1975 |
| EP | 0 516 401 A1 | 12/1992 |
| WO | WO99/57558 | 11/1999 |

OTHER PUBLICATIONS

"Heterogenous Catalytic Reactions involving Molecular Oxygen" G.I. Galodets, Elsevier, Amsterdam 1983 pp. 229-278.
"Oxygen in Catalysis", A. Bielanski et al., New York, 1991, pp. 181-210.
"Parts-Per-Trillion Moisture Measurement Using Cavity Ring-Down Spectroscopy", Wen-Bin Yan, Jul.-Aug. 2002, Gases and Technology, pp. 21-24.
Brochure by TigerOptics "MTO-1000-CH$_4$".
Brochure by TigerOptics "MTO-1000-H$_2$0".
International Search Report PCT /US03/23571, dated Dec. 23, 2003.

* cited by examiner

*Primary Examiner*—Brian Sines
(74) *Attorney, Agent, or Firm*—RatnerPrestia

(57) ABSTRACT

A device and method for quantifying an impurity in an input gas stream. The device and method employ a catalyst to convert the impurity to a detectable species in an output gas stream, and the concentration of the detectable species is then measured by means of a detector.

33 Claims, 1 Drawing Sheet

ANALYTICAL SENSITIVITY ENHANCEMENT BY CATALYTIC TRANSFORMATION

FIELD OF THE INVENTION

This invention relates to analysis of impurities in a gas sample. More particularly, it relates to the use of a catalyst to increase the sensitivity of detection of impurities in a gas sample.

BACKGROUND OF THE INVENTION

In many industrial processes, the concentration of trace species in flowing gas streams and liquids must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities—even at parts per billion (ppb) levels—is damaging and reduces the yield of operational circuits. Therefore, the relatively high sensitivity with which such impurities can be monitored is important to manufacturers of high-purity gases used in the semiconductor industry. Various impurities must be detected in other industrial applications as well. For many of these analytical applications, spectroscopic techniques are preferred due to their high sensitivity and rapidity of measurement, making possible real-time quantitation of impurities.

As an analytical technique, absorption-type spectroscopy offers high sensitivity, response times on the order of microseconds, immunity from poisoning, and limited interference from molecular species other than the species under study. Various molecular species can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

Spectroscopy has obtained parts per million (ppm) level detection for gaseous contaminants in high-purity gases. Detection sensitivities at the ppb level are attainable in some cases. Accordingly, several spectroscopic methods have been applied to such applications as quantitative contamination monitoring in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In recent years, a spectroscopic technique known as cavity ring-down spectroscopy (CRDS) has become an important spectroscopic technique with applications to science, industrial process control, and atmospheric trace gas detection. CRDS has been demonstrated as a technique for the measurement of optical absorption that excels in the low-absorbance regime where conventional methods have inadequate sensitivity. CRDS utilizes the mean lifetime of photons in a high-finesse optical resonator as the absorption-sensitive observable.

Typically, the resonator is formed from a pair of nominally equivalent, narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CRDS is determined by the magnitude of the intrinsic resonator losses, which can be minimized with techniques such as superpolishing that permit the fabrication of ultralow-loss optics.

Various novel approaches to mirror based CRDS systems are provided in U.S. Pat. Nos. 5,973,864, 6,097,555, 6,172,823 B1, and 6,172,824 B1 issued to Lehmann et al., and incorporated herein by reference. These approaches teach the use of a near-confocal resonator formed by two reflecting elements or prismatic elements.

Although, when compared with the other spectroscopy methods, ring down cavity spectroscopy is simpler and less expensive to implement, and has a very high level of sensitivity for detecting certain materials, it may still not provide sufficient sensitivity for certain species when present at very low concentrations.

Thus, there continues to be a need for analytical techniques allowing convenient quantitation of certain species present in gas samples at very low concentrations.

SUMMARY OF THE INVENTION

In view of the shortcomings of the prior art, the invention provides devices and methods for achieving high levels of sensitivity in the analysis of an impurity in a gas stream.

In one aspect, the invention is a device for determining a level of concentration of an impurity in an input gas stream. The device comprises a catalytic converter comprising a catalyst, the catalyst selected to convert substantially all of the impurity into a detectable species in an output gas stream, and a detector coupled to the catalytic converter and adapted to determine a level of concentration of the detectable species in the output gas stream.

In another aspect, the invention is a method for determining a level of concentration of an impurity in an input gas stream by use of a catalytic converter comprising a catalyst. The method comprises the steps of inputting the input gas stream into the catalytic converter; converting the impurity into a detectable species in an output gas stream; and detecting a presence of the detectable species in the output gas stream.

In yet another aspect, the invention is a device for determining a level of concentration of an impurity in an input gas stream. The device comprises a catalytic converter comprising a catalyst for converting substantially all of the impurity into a detectable species in an output gas stream, input means for inputting the input gas stream into the catalytic converter; and detecting means for detecting a presence of the detectable species in the output gas stream.

DETAILED DESCRIPTION OF THE INVENTION

Figure 1:
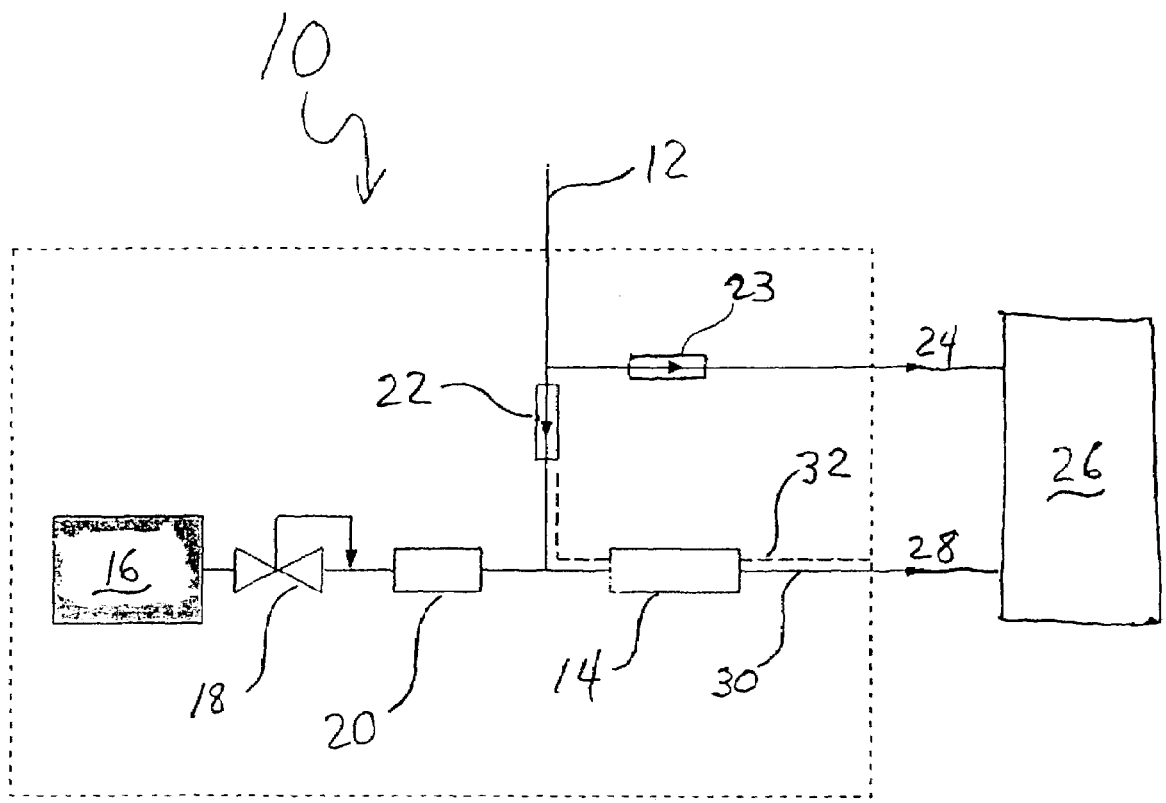
FIG. 1 is a schematic representation of an exemplary device, according to the invention.

The entire disclosure of U.S. patent application Ser. No. 10/017,367 filed Dec. 12, 2001; U.S. patent application Ser. No. 10/157,400 filed May 29, 2002; and U.S. Pat. Nos. 5,528,040; 5,973,864; 6,097,555; 6,172,823 B1; and 6,172,824 B1 are expressly incorporated herein by reference.

The invention will next be illustrated with reference to the FIGURE, which is intended to be illustrative rather than limiting and is included herewith to facilitate the explanation of the invention. The FIGURE is not to scale, and is not intended as an engineering drawing.

The invention provides devices and methods for quantitatively determining the concentration of impurities at low levels in gas streams. In general, the devices and methods involve passing the gas stream through a converter that catalytically converts the impurity to a detectable species, whose concentration is then measured by a suitable detector attached to the converter by typical gas handling devices such as connectors, valves, regulators, and tubes or pipes. The technique is applicable to measuring concentrations of a variety of impurities, and the type and concentration of impurity are two determining factors in picking the type and construction of the converter, as well as picking the type of detector.

Referring now to FIG. 1, there is shown an exemplary embodiment of the invention providing a device 10 for determining a concentration of oxygen in an input gas stream 12. Such input gas streams may be used for example in semiconductor processing. Nonlimiting examples of gases in which oxygen may be detected may include for example nitrogen, helium, argon, and hydrogen, but others may also be used.

The device 10 comprises a catalytic converter 14 including a chamber containing a catalyst (not shown). The chamber may be constructed from any material suitable for gas handling, provided that the chamber itself does not alter the amount of oxygen in the input gas stream. The entire chamber may be constructed from a material that is inert, under the conditions of use, to oxygen. It may be inert as well to other components present in the input gas stream. Alternatively, the chamber may merely be lined internally with such a material. Nonlimiting examples of such materials include quartz and copper. In one exemplary embodiment, the chamber is constructed essentially of copper.

The exact size and dimensions of the chamber are not critical to the practice of the invention, provided that there is sufficient contact time between the oxygen in the input gas and the catalyst (described below) to ensure that essentially all of the oxygen is converted into water. In one exemplary embodiment, the chamber is a copper tube. The inside diameter of the tube is typically from about 1 mm to about 20 mm, and the length of the tube is typically from about 2 cm to about 100 cm. In one exemplary embodiment, the inside diameter is about 3/16" (about 4.8 mm) and the length is about 20 inches.

The chamber contains a catalyst selected to convert substantially all of the oxygen in the input gas stream into water, which will subsequently be detected by an appropriate detector. Any catalyst that effectively provides conversion of the oxygen in the input gas stream into water, by combination with hydrogen, may be used in accordance with the invention. The physical configuration of the catalyst may encompass essentially any particle size or shape, including for example beads, fibers, irregular particulates, spun configurations, or other shapes and sizes, provided that when enclosed within the chamber they allow sufficient gas flow through the catalytic converter 14, as described below. Nonlimiting examples of suitable catalysts include nickel, especially nickel wool or nickel gauze. An exemplary nickel wool having a diameter of about 0.038 mm is available from Exeter Analytical Inc. of N. Chelmsford, Mass. A suitable nickel gauze (100 mesh, with a wire diameter of 0.114 mm) is available from Alfa Aesar of Ward Hill, Mass. Other suitable catalytic materials for conversion of oxygen into water are known to those skilled in the catalyst art, and may include, as nonlimiting examples, platinum and palladium. The chamber may contain other materials in addition to the catalyst, provided they do not interfere substantially with the conversion of oxygen into water, and do not interfere with the accurate analysis of the water as it exits the chamber in the output gas stream.

A hydrogen source 16 is coupled to the catalytic converter 14 in a manner adapted to provide contact between hydrogen and the catalyst, thereby providing an active catalyst surface that the oxygen can contact, for conversion into water. Alternatively, in one exemplary embodiment, the hydrogen source is the catalyst itself and includes pre-adsorbed hydrogen. An example of such a catalyst/hydrogen source with pre-adsorbed hydrogen is Raney® pre-hydrogenated nickel, available from Sigma-Aldrich Corp., St. Louis, Mo. Such a combined catalyst/hydrogen source may be used alone, or in conjunction with an additional source of hydrogen gas. In the case of Raney® pre-hydrogenated nickel, which typically is commercially available in an aqueous medium, removal of water must be performed before the catalyst is used for oxygen analysis, for example by vacuum drying and/or passing a dry nitrogen or hydrogen gas stream over the nickel.

Hydrogen source 16, which may provide either essentially pure hydrogen or a mixture of hydrogen with a diluent gas such as nitrogen, helium, or argon, for example, may also comprise a tank (not shown). Alternatively, in another exemplary embodiment of the invention, the hydrogen source 16 is a hydrogen generator. Such hydrogen generators are known in the art, and commercially available from such companies as Matheson Tri-Gas of Irving, Tex. and Scott Specialty Gases of Plumsteadville, Pa. Such a hydrogen generator typically provides a source of very pure hydrogen having a very low content of oxygen and, thus, is especially suitable for use according to the invention.

The hydrogen or hydrogen mixture from hydrogen source 16 is fed into the catalytic converter 14, typically near the point where the input gas stream 12 enters the converter, and may be metered in (in amounts to be described below) by means of standard metering devices known in the gas-handling art. As shown in FIG. 1, a regulator 18 may be used to provide a convenient pressure of hydrogen, and a mass flow controller 20 may be used to meter in the desired amount of gas per unit time. Although FIG. 1 shows the use of a regulator 18 and a mass flow controller 20, either or both of these may be absent, or alternative flow-control devices may be used. In general, any source of hydrogen of sufficient purity may be used.

The required level of hydrogen purity varies according to the level of oxygen in the input gas stream, and on the level of accuracy and precision required for the measurement. The hydrogen should not contain amounts of any catalyst-poisoning material sufficient to substantially affect the activity of the catalyst. Such catalyst-poisoning materials are well known to those skilled in the catalyst art, and incldue for example hydrogen sulfide. The hydrogen should contain as little oxygen as possible, to minimize interference with the measurement of the oxygen in the input gas stream. Typically, for analysis of input gas steams having an oxygen content of up to about 2.5 ppm, the oxygen content contributed to the gas stream by the hydrogen source is preferably below about 0.1 ppb. Thus if for example a 0.5% level of hydrogen is present in the gas stream as it enters the catalytic converter 14, the hydrogen source preferably contains less than about 0.1 ppb/0.5%=20 ppb of oxygen. Higher levels may be acceptable in some situations, although they may result in reduced measurement sensitivity.

In addition, the sensitivity and accuracy of the measurement is affected by the amount of water (if any) already present in the input gas stream, and high levels lead to loss of sensitivity. Therefore, water in the gas sample itself may be removed by any convenient means, provided that such means do not interfere with the measurement, for instance by trapping oxygen. Such means of water removal may include a commercially available moisture trap (not shown) such as the model SS-70KF-N-4R purifier, available from Aeronex, San Diego, Calif. By the same token, water that may be adventitiously introduced by way of the carrier gas or the hydrogen source will also reduce the sensitivity and precision of the measurement, and thus should be minimized. In general, for a detector having an innate upper oxygen detection limit of L (in parts per million, or other units), the actual upper detection limit $L(A)$ is given by the equation $L(A)=L-(B/2)$, where B is the background level of water in the output gas stream. The background water level B may conveniently be measured by running the measurement twice, once with and once without catalytic conversion of oxygen into water.

In one exemplary embodiment of the invention, shown in FIG. 1, device 10 may comprise a check valve 22, and optionally a second check valve 23, both of which prevent backflow of gases. By such an arrangement, the input gas stream 12 containing the oxygen to be measured can be directed without catalytic conversion to the detector 26, thereby allowing measurement of the background water, as well as to the catalytic converter 14. An output gas stream from the catalytic converter 14 then flows along path 28 to the detector 26. By means of this arrangement, pre- and post-conversion levels of water can be determined, and a background level thereby calculated. The pre-conversion level may be determined before the post-conversion level, after it, or simultaneously. In addition, although elements 22 and 23 may be check valves, it is contemplated that a unidirectional flow control, such as a flow switch, may be substituted for either or both of check valves 22 and 23, and under the control of a process controller (not shown).

In another alternative embodiment of the invention, valves 22 and 23 may be operated such that input gas 12 is split between paths 24 and 28, with measurements of water level being performed simultaneously by the detector 26, in the case where the detector is adapted to perform simultaneous measurements. Although FIG. 1 shows an embodiment employing check valves 22 and 23, other gas-handling configurations may be used to provide measurement of both background water and water derived from conversion of oxygen into water. In yet another exemplary embodiment, no provision is made for measurement of background water, and only the output gas stream from the catalytic converter 14 is fed to the detector 26. Such an arrangement may, for example, be suitable for applications where it is known that the background level of water in input gas stream 12 is negligible, or the concentration level is already known.

The detector 26 is coupled to the catalytic converter 14 and adapted to determine a level of concentration of water in the output gas stream. The detector 26 can be of any type that is suitable for measuring low concentrations of water in a gas stream, and may include for example an electrochemical cell. Suitable examples of such an electrochemical cell are available from Meeco, Inc. of Warrington, Pa., and sold under the names Tracer, Aquavolt, and Accupoint. Depending upon the exact electrochemical cell detector chosen, water contents in the output gas stream can be measured with a lower detection limit as low as 1 ppb and as high as 20 ppm.

The detector 26 may be adapted to measure absorption of electromagnetic radiation, for example infrared radiation. As used herein, the term "infrared radiation" means radiation in any or all of the near infrared, mid-infrared, and far infrared regions of the spectrum. For example a Fourier Transform infrared spectrometer may be used; such spectrometers are well known in the analytical art and widely available commercially in a variety of configurations and models. In one exemplary embodiment, the detector 26 comprises a Cavity Ring Down Spectrometer (CRDS). Such detectors are described for example in U.S. Pat. No. 5,528,040 to Lehmann, and U.S. Pat. Nos. 5,973,864, 6,097,555, 6,172,823 B1, and 6,172,824 B1, all issued to Lehmann et al. Also suitable are CRDS spectrometers such as are commercially available from Tiger Optics L.L.C. of Warrington, Pa., a suitable example of which is sold under the name of MTO-1000. By use of a CRDS detector, very high sensitivity can be obtained. For example, oxygen levels between about 200 ppt (parts per trillion) and 2.5 ppm (parts per million) can be quantified, according to the invention. Higher levels of oxygen concentration can also be measured using a CRDS detector if the input gas stream 12 is first diluted with a carrier gas such as for example nitrogen, helium, argon, or hydrogen.

In operation, a device 10 for measuring oxygen content of an input gas stream 12 according to the invention should provide enough hydrogen to assure that essentially all of the oxygen in the input gas stream is converted into water. In general, the amount of hydrogen supplied to the input gas stream 12 should represent a large excess relative to oxygen. The partial volume ratio of hydrogen to oxygen may be in a range of about 500:1 or higher, in order to assure complete conversion. A typical ratio may be about 2000:1. For example, about a 0.5% hydrogen content may be used in an application where the oxygen level is expected to be about 2.5 ppm.

Substantially larger ratios of hydrogen to oxygen may be used, and in fact pure hydrogen without an inert carrier gas may be used. Use of such high amounts of hydrogen may be limited mainly by the desire to avoid increasing the input of whatever impurities accompany the hydrogen, to avoid a potential flammability hazard due to emission of unreacted hydrogen from the device, and to avoid unnecessary costs due to hydrogen wastage. Typically, for measurement of oxygen levels up to about 2.5 ppm, the hydrogen content of the input gas stream 12 before reaction may be about 0.25% to about 4%, and typically about 0.5%.

In order for the device 10 to provide sufficiently rapid and complete conversion of oxygen into water, and to prevent water from condensing prior to reaching the detector and therefore not being measured, elevated temperatures may be provided in the catalytic converter 14 and in any connecting parts conveying the output gas stream to the detector 26. Typically, if a nickel catalyst is used, the temperature of the catalytic converter 14 is maintained in a range of about 200° C. to about 500° C., most typically about 200° C. to about 250° C. Preferably, a temperature of about 200° C. is used.

Temperatures significantly below about 200° C. tend to result in incomplete conversion of oxygen into water, and temperatures above about 500° C. have been found to result, in at least some cases, in inhibition of the conversion, as well as combination of nickel with oxygen, leading to incorrectly low indications of oxygen concentration. Heating of the catalytic converter 14 may be achieved by any convenient means (not shown), such as an oven or by use of electrical resistance tape.

Connecting parts 30 joining the catalytic converter and the detector may also be heated, typically in a range of about 60° C. to about 100° C., most typically about 80° C., to prevent loss of water by condensation. Heating may be achieved by any convenient means, including for example the use of electrical heating tape 32. Such connecting parts 30 may for example comprise electropolished stainless steel. For such materials a temperature above about 100° C. may give rise to generation of moisture by interaction of hydrogen with the stainless steel, and therefore will typically be avoided. Alternatively, the connecting parts may be made of copper, or lined with copper. Heating, for example by use of heating tape, may also be provided upstream of the catalytic converter 14, in order to preheat the incoming gas stream.

In order for essentially complete conversion of oxygen into water to occur, there must be sufficient residence time of the input gas in the catalytic converter 14. Thus, the flow rate of the input gas stream 12 through the catalytic converter 14 must not be too fast. Suitable flow rates in SCCM (Standard Cubic Centimeters per Minute) depend upon the inside diameter and length of the chamber, the volume percent of free space (gas phase space) inside the chamber, and the surface area and catalytic activity of the catalyst. Other factors may also contribute. Typically, a space velocity of input gas stream 12 through catalytic converter 14 between about 5 and about 220 seconds$^{-1}$ is suitable, where space velocity is defined as the ratio of volumetric flow rate to catalyst volume. Suitable flow rates can be readily discerned by the skilled artisan with a minimum of experimentation, but for example may be between about 50 and about 2000 SCCM, corresponding to a space velocity between about 5 and about 220 seconds$^{-1}$, for a ¼" outside diameter (about 3/16" inside diameter) copper tube of about 10 to about 20 inches length, packed with about 1.5 grams of nickel wool (about 0.038 mm diameter) as the catalyst, and operating at about 200° C.

In another embodiment of the invention, the device and method as described above for the measurement of oxygen may be adapted for the analysis of ozone, or mixtures of oxygen and ozone. Essentially the same construction, conditions and operating parameters for the device may be used as for the measurement of oxygen as outlined above.

Although the invention is described herein with reference to specific embodiments, the invention is not intended to be limited to the details shown. Rather, various modifications may be made in the details within the scope and range of equivalents of the claims and without departing from the invention.

What is claimed:

1. A device for determining a level of concentration of at least one of oxygen or ozone in an input gas stream, the device comprising:
    a catalytic converter comprising a catalyst, the catalyst capable of converting substantially all of the oxygen or ozone into water in an output gas stream; and
    a detector coupled to the catalytic converter and adapted to determine a level of concentration of the water in the output gas stream, wherein the detector comprises a cavity ring-down spectrometer.
2. The device of claim 1, wherein the catalyst is capable of converting oxygen into water.
3. The device of claim 1, wherein the catalyst is capable of converting ozone into water.
4. The device of claim 1, wherein the catalyst comprises nickel.
5. The device of claim 4, wherein the nickel comprises at least one of nickel wool and nickel gauze.
6. The device of claim 1, wherein the catalytic converter comprises a chamber containing the catalyst, the chamber having an inner surface consisting essentially of an inert material.
7. The device of claim 6, wherein the inert material comprises copper.
8. A device for determining a level of concentration of an impurity in an input gas stream, the device comprising:
    a catalytic converter comprising a catalyst, the catalyst selected to convert substantially all of the impurity into a detectable species in an output gas stream:
    a detector coupled to the catalytic converter and adapted to determine a level of concentration of the detectable species in the output gas stream, wherein the detector comprises a cavity ring-down spectrometer; and
    a hydrogen source coupled to the catalytic converter to provide a contact between hydrogen and the catalyst.
9. The device of claim 8, wherein the hydrogen source comprises a hydrogen generator.
10. The device of claim 8, wherein the hydrogen source comprises hydrogen pre-adsorbed on the catalyst.
11. A method for determining a level of concentration of at least one of oxygen or ozone in an input gas stream by use of a catalytic converter comprising a catalyst, the method comprising:
    inputting the input gas stream into the catalytic converter;
    converting the oxygen or ozone in the catalytic converter into water in an output gas stream; and
    detecting a presence of the water in the output gas stream by means of a cavity ring-down spectrometer.
12. The method of claim 11 further comprising detecting a presence of a background level of the water in the input gas stream either prior to the inputting step or substantially simultaneous with the inputting step.
13. The method of claim 11, wherein the detecting further comprises determining a level of concentration of the water.
14. The method of claim 11, wherein the converting comprises converting oxygen.
15. The method of claim 11, wherein the converting comprises converting ozone.
16. The method of claim 11, wherein the catalyst comprises nickel.
17. The method of claim 16, wherein the nickel comprises at least one of nickel wool and nickel gauze.
18. The method of claim 11, wherein the catalytic converter comprises a chamber having an inner surface consisting essentially of an inert material, the catalyst contained within the chamber.
19. The method of claim 18, wherein the inert material comprises copper.
20. A method for determining a level of concentration of an impurity in an input gas stream by use of a catalytic converter comprising a catalyst, the method comprising:
    inputting the input gas stream into the catalytic converter;
    converting the impurity into a detectable species in an output gas stream;

detecting a presence of the detectable species in the output gas stream by means of a cavity ring-down spectrometer;

providing a hydrogen source; and coupling the hydrogen source to the catalytic converter to provide a contact between hydrogen and the catalyst.

21. The method of claim 20, wherein the providing the hydrogen source comprises providing a hydrogen generator.

22. The method of claim 20, wherein the providing the hydrogen source comprises pre-absorbing hydrogen on the catalyst.

23. A device for determining a level of concentration of at least one of oxygen or ozone in an input gas stream, the device comprising:

a catalytic converter comprising a catalyst of converting substantially all capable of the oxygen or ozone into water in an output gas stream;

input means for inputting the input gas stream into the catalytic converter; and detecting means for detecting a presence of the water in the output gas stream, said detecting means comprising a cavity ring-down spectrometer.

24. The device of claim 23, wherein the catalyst is capable of converting oxygen into water.

25. The device of claim 23, wherein the catalyst is capable of converting ozone into water.

26. The device of claim 23, further comprising a hydrogen source coupled to the catalytic converter to provide a contact between hydrogen and the catalyst.

27. The device of claim 23, wherein the catalyst comprises nickel.

28. The device of claim 27, wherein the nickel comprises at least one of nickel wool and nickel gauze.

29. The device of claim 23, wherein the catalytic converter comprises delivery means for delivering substantially all of the oxygen or ozone to the catalyst without loss prior to the delivering.

30. The device of claim 29, wherein the delivery means comprises a chamber having an inner surface consisting essentially of an inert material, the catalyst contained within the chamber.

31. The device of claim 29, wherein the inert material comprises copper.

32. A device for determining a concentration of an impurity in an input gas stream, the device comprising:

a catalytic converter comprising a catalyst for converting substantially all of the impurity into a detectable species in an output gas stream;

input means for inputting the input gas stream into the catalytic converter;

detecting means for detecting a presence of the detectable species in the output gas stream, said detecting means comprising a cavity ring-down spectrometer;

a hydrogen generator coupled to the catalytic converter to provide a contact between hydrogen and the catalyst.

33. A device for determining a concentration of an impurity in an input gas stream, the device comprising:

a catalytic converter comprising a catalyst for converting substantially all of the impurity into a detectable species in an output gas stream;

input means for inputting the input gas stream into the catalytic converter;

detecting means for detecting a presence of the detectable species in the output gas stream, said detecting means comprising a cavity ring-down spectrometer; and a hydrogen source coupled to the catalytic converter to provide a contact between hydrogen and the catalyst, wherein the catalyst comprises hydrogen pre-absorbed thereon.

* * * * *